(12) United States Patent (10) Patent No.: US 10,238,764 B2
Trzecieski (45) Date of Patent: Mar. 26, 2019

(54) AROMATHERAPY VAPORIZATION DEVICE

(71) Applicant: Michael Trzecieski, Toronto (CA)

(72) Inventor: Michael Trzecieski, Toronto (CA)

(73) Assignee: Vapium Inc., Toronto (CA)

( * ) Notice: Subject to any disclaimer, the term of this patent is extended or adjusted under 35 U.S.C. 154(b) by 730 days.

(21) Appl. No.: 14/829,660

(22) Filed: Aug. 19, 2015

(65) Prior Publication Data

US 2016/0051464 A1 Feb. 25, 2016

Related U.S. Application Data

(60) Provisional application No. 62/038,863, filed on Aug. 19, 2014.

(51) Int. Cl.
| | |
|---|---|
| *A61M 15/00* | (2006.01) |
| *H05B 3/42* | (2006.01) |
| *H05B 3/44* | (2006.01) |
| *A61L 9/03* | (2006.01) |
| *H05B 3/03* | (2006.01) |
| *A61M 15/08* | (2006.01) |

(Continued)

(52) U.S. Cl.
CPC .............. *A61L 9/03* (2013.01); *A61M 11/003* (2014.02); *A61M 11/042* (2014.02); *A61M 15/08* (2013.01); *H05B 3/03* (2013.01); *H05B 3/42* (2013.01); *A61M 15/06* (2013.01); *A61M 2205/8206* (2013.01)

(58) Field of Classification Search
None
See application file for complete search history.

(56) References Cited

U.S. PATENT DOCUMENTS 3,513,859 A 5/1970 Carty
3,707,017 A 12/1972 Paquette
(Continued)

FOREIGN PATENT DOCUMENTS

EP 2253233 11/2010
WO 2009027959 A1 3/2009
(Continued)

OTHER PUBLICATIONS

Document relating to U.S. Appl. No. 14/614,005, dated Oct. 20, 2017 (Office Action).
(Continued)

*Primary Examiner* — Joseph M Pelham
(74) *Attorney, Agent, or Firm* — Bereskin & Parr LLP/S.E.N.C.R.L., s.r.l.

(57) ABSTRACT

A novel herbal vaporization device (HVD) and method is disclosed. The HVD includes a recharging unit for storing therein of a vaporization unit having a heating chamber disposed at a first end thereof for receiving of loose leaf herbal material and for providing of heat thereto, the vaporization unit comprising a second end disposed opposite the first end with a fluid pathway between the two ends. In a first mode of operation the vaporization unit is for being recharged from the recharging unit and in a second mode of operation the vaporization unit is for use in vaporizing of loose leaf herbal material inserted into the heating chamber for having at least partially vaporized loose leaf herbal material and ambient air to flow through the fluid pathway.

13 Claims, 4 Drawing Sheets

(51) Int. Cl.
*A61M 11/00* (2006.01)
*A61M 11/04* (2006.01)
*A61M 15/06* (2006.01)

(56) References Cited

U.S. PATENT DOCUMENTS

| | | | |
|---|---|---|---|
| 4,774,970 A | 10/1988 | Bell | |
| 5,144,962 A | 9/1992 | Counts et al. | |
| 5,261,601 A | 11/1993 | Ross et al. | |
| 5,269,327 A | 11/1993 | Counts et al. | |
| 5,273,190 A | 12/1993 | Lund | |
| 5,591,368 A | 1/1997 | Fleischhauer et al. | |
| 5,865,185 A | 2/1999 | Collins et al. | |
| 6,125,853 A | 10/2000 | Susa et al. | |
| 6,446,426 B1 | 9/2002 | Sweeny et al. | |
| 6,513,524 B1 | 2/2003 | Storz | |
| 6,761,164 B2 | 7/2004 | Amirpour et al. | |
| 6,772,756 B2 | 8/2004 | Shayan | |
| 6,810,883 B2 | 11/2004 | Felter et al. | |
| 6,990,978 B2 | 1/2006 | Shayan | |
| 7,088,914 B2 | 8/2006 | Whittler et al. | |
| 7,100,618 B2 | 9/2006 | Dominguez | |
| 7,141,215 B2 | 11/2006 | Guan et al. | |
| 7,186,958 B1 | 3/2007 | Nelson | |
| 7,434,584 B2 | 10/2008 | Steinberg | |
| 7,445,007 B2 | 11/2008 | Balch et al. | |
| 7,475,684 B2 | 1/2009 | Balch et al. | |
| 7,524,734 B2 | 12/2009 | Balch et al. | |
| 7,665,460 B2 | 2/2010 | Lindsay et al. | |
| 7,726,308 B1 | 6/2010 | Flora | |
| 7,826,726 B2 | 11/2010 | McCoy | |
| 8,371,310 B2 | 2/2013 | Brenneise | |
| 8,387,612 B2 | 3/2013 | Damani et al. | |
| 8,483,552 B2 | 7/2013 | Durisek | |
| 8,488,952 B2 | 7/2013 | Landry | |
| 8,517,010 B2 | 8/2013 | Power et al. | |
| 8,550,091 B2 | 10/2013 | Yomtov et al. | |
| 8,739,786 B2 | 6/2014 | Postma | |
| 8,781,306 B2 | 7/2014 | Hatten | |
| 8,863,752 B2 | 10/2014 | Hon | |
| 8,869,792 B1 * | 10/2014 | Lee | A61M 15/06 128/202.21 |
| 8,881,737 B2 | 11/2014 | Collett et al. | |
| 8,899,230 B2 | 12/2014 | Immel | |
| 8,910,630 B2 | 12/2014 | Todd | |
| 8,991,402 B2 | 3/2015 | Bowen et al. | |
| 2003/0154991 A1 | 8/2003 | Fournier et al. | |
| 2003/0196661 A1 | 10/2003 | Miekka et al. | |
| 2005/0261641 A1 | 11/2005 | Warchol et al. | |
| 2006/0054165 A1 | 3/2006 | Hughes | |
| 2006/0102175 A1 | 5/2006 | Nelson | |
| 2006/0175425 A1 | 8/2006 | McGee et al. | |
| 2006/0283449 A1 | 12/2006 | Balch et al. | |
| 2007/0045268 A1 | 3/2007 | Nelson | |
| 2007/0045288 A1 | 3/2007 | Nelson | |
| 2007/0068523 A1 | 3/2007 | Fishman | |
| 2007/0102013 A1 | 5/2007 | Adams et al. | |
| 2007/0125765 A1 | 6/2007 | Nelson | |
| 2007/0175476 A1 | 8/2007 | Lipowicz | |
| 2007/0240706 A1 | 10/2007 | Kobayashi et al. | |
| 2007/0280652 A1 | 12/2007 | Williams | |
| 2008/0023003 A1 | 1/2008 | Rosenthal | |
| 2008/0149118 A1 | 6/2008 | Oglesby et al. | |
| 2009/0078253 A1 | 3/2009 | Bao | |
| 2009/0283103 A1 | 11/2009 | Nielsen et al. | |
| 2009/0293892 A1 | 12/2009 | Williams et al. | |
| 2009/0302019 A1 | 12/2009 | Selenski et al. | |
| 2009/0320863 A1 | 12/2009 | Fernando et al. | |
| 2010/0006113 A1 | 1/2010 | Urtsev et al. | |
| 2010/0012118 A1 | 1/2010 | Storz | |
| 2010/0074603 A1 | 3/2010 | Balch et al. | |
| 2010/0119606 A1 | 5/2010 | Whittle et al. | |
| 2010/0126516 A1 | 5/2010 | Yomtov et al. | |
| 2010/0200006 A1 | 8/2010 | Robinson et al. | |
| 2010/0322599 A1 | 12/2010 | Landry | |
| 2011/0005535 A1 | 1/2011 | Xiu | |
| 2011/0036346 A1 | 2/2011 | Cohen et al. | |
| 2011/0041840 A1 | 2/2011 | Dunne | |
| 2011/0094523 A1 | 4/2011 | Thorens et al. | |
| 2011/0126831 A1 | 6/2011 | Fernandez Pernía | |
| 2011/0226266 A1 | 9/2011 | Tao | |
| 2011/0236002 A1 | 9/2011 | Oglesby et al. | |
| 2011/0277761 A1 | 11/2011 | Terry | |
| 2011/0278189 A1 * | 11/2011 | Terry | A24F 47/008 206/459.1 |
| 2011/0290269 A1 | 12/2011 | Shimizu | |
| 2011/0297166 A1 | 12/2011 | Takeuchi et al. | |
| 2012/0037154 A1 | 2/2012 | Gallem et al. | |
| 2012/0070134 A1 | 3/2012 | Durisek | |
| 2012/0077849 A1 | 3/2012 | Howson et al. | |
| 2012/0085344 A1 | 4/2012 | Luber et al. | |
| 2012/0199663 A1 | 8/2012 | Qui | |
| 2012/0204889 A1 | 8/2012 | Kiu | |
| 2012/0234821 A1 | 9/2012 | Shimizu | |
| 2012/0255546 A1 | 10/2012 | Goetz et al. | |
| 2012/0255567 A1 * | 10/2012 | Rose | A61K 9/12 131/273 |
| 2012/0269497 A1 | 10/2012 | Hatten | |
| 2012/0318882 A1 | 10/2012 | Abehasera | |
| 2012/0304990 A1 | 12/2012 | Todd | |
| 2012/0325227 A1 | 12/2012 | Robinson et al. | |
| 2013/0037041 A1 | 2/2013 | Worm et al. | |
| 2013/0042865 A1 | 2/2013 | Monsees et al. | |
| 2013/0087144 A1 | 4/2013 | Todd | |
| 2013/0139813 A1 | 6/2013 | Storz | |
| 2013/0152922 A1 | 6/2013 | Benassayag et al. | |
| 2013/0167853 A1 | 7/2013 | Lui | |
| 2013/0174842 A1 | 7/2013 | Young et al. | |
| 2013/0206154 A1 | 8/2013 | Fernando et al. | |
| 2013/0233309 A1 | 9/2013 | Todd | |
| 2013/0247910 A1 | 9/2013 | Postma | |
| 2013/0251354 A1 | 9/2013 | Durisek | |
| 2013/0298905 A1 * | 11/2013 | Levin | A24F 47/008 128/202.21 |
| 2013/0319435 A1 | 12/2013 | Flick | |
| 2014/0014125 A1 | 1/2014 | Fernando et al. | |
| 2014/0041655 A1 * | 2/2014 | Barron | A61M 11/042 128/202.21 |
| 2014/0064713 A1 | 3/2014 | Niemiec et al. | |
| 2014/0069424 A1 | 3/2014 | Poston et al. | |
| 2014/0144429 A1 | 5/2014 | Wensley et al. | |
| 2014/0196736 A1 | 7/2014 | Fernando et al. | |
| 2014/0209109 A1 | 7/2014 | Larson | |
| 2014/0251355 A1 | 9/2014 | Tracey | |
| 2014/0283824 A1 | 9/2014 | Wheelock et al. | |
| 2014/0283855 A1 | 9/2014 | Hawes et al. | |
| 2014/0299141 A1 | 10/2014 | Flick | |
| 2014/0314397 A1 | 10/2014 | Alima | |
| 2014/0318559 A1 | 10/2014 | Thorens et al. | |
| 2014/0345633 A1 | 11/2014 | Talon et al. | |
| 2014/0360517 A1 | 12/2014 | Taggert et al. | |
| 2014/0366898 A1 * | 12/2014 | Monsees | A24F 47/008 131/329 |
| 2014/0366900 A1 | 12/2014 | Plojoux et al. | |
| 2014/0373857 A1 | 12/2014 | Steinberg | |
| 2015/0020825 A1 * | 1/2015 | Galloway | A24F 47/008 131/329 |
| 2015/0020832 A1 | 1/2015 | Greim et al. | |
| 2015/0027469 A1 | 1/2015 | Tucker et al. | |
| 2015/0040930 A1 | 2/2015 | Robinson et al. | |
| 2015/0101606 A1 * | 4/2015 | White | A61M 15/00 128/203.26 |
| 2015/0150305 A1 * | 6/2015 | Shenkal | A24F 47/008 131/329 |
| 2015/0163859 A1 | 6/2015 | Schneider et al. | |
| 2015/0217064 A1 | 8/2015 | Trzecieski | |
| 2015/0223520 A1 | 8/2015 | Phillips et al. | |
| 2015/0282525 A1 | 10/2015 | Plojoux et al. | |
| 2015/0351456 A1 | 12/2015 | Johnson et al. | |
| 2016/0213066 A1 | 7/2016 | Zitzke et al. | |
| 2016/0331912 A1 * | 11/2016 | Trzecieski | A61M 11/042 |
| 2017/0065776 A1 * | 3/2017 | Trzecieski | A61M 11/042 |
| 2017/0095623 A1 * | 4/2017 | Trzecieski | A61M 11/042 |

(56) References Cited

U.S. PATENT DOCUMENTS

2017/0181471 A1\* 6/2017 Phillips ................. H02J 7/0029
2017/0303597 A1\* 10/2017 Tsui ..................... A24F 47/008
2017/0360091 A1\* 12/2017 Bless ................... A24F 47/008
2018/0070647 A1\* 3/2018 Monsees ............... A24F 47/008

FOREIGN PATENT DOCUMENTS

WO     2013098405 A2    7/2013
WO     2013098411 A1    7/2013

OTHER PUBLICATIONS

Document relating to U.S. Appl. No. 14/614,005, dated May 17, 2018 (Office Action).

\* cited by examiner

AROMATHERAPY VAPORIZATION DEVICE

CROSS REFERENCE TO RELATED APPLICATION

This application benefits from the priority of U.S. Provisional Applications 62/038,863 filed on Aug. 19, 2014, which is incorporated herein by reference.

TECHNICAL FIELD OF THE INVENTION

The technical field relates to a device for vaporization of phyto materials and more specifically to a device for aromatherapy vaporization.

BACKGROUND OF THE INVENTION

Aromatherapy generally uses essential oils, which are extracted from phyto materials, such as leaves of plants, for therapeutic benefits. These essential oils are either massaged into the skin or can be inhaled. In some cases the phyto materials are heated in order to released the essential oils therefrom. By heating these phyto materials at predetermined temperatures, essential oils and extracts are boiled off, depending upon the temperature at which these phyto materials are heated, an aroma or vapor is given off, which is then inhaled by a user for its therapeutic benefits. Devices that provide such operation are generally known as vaporizers. Different phyto materials release vapors at different temperatures. Some release vapors at 120 degrees Celsius, whereas others at 220 degrees Celsius. Ideally the predetermined temperature is less than a combustion temperature of the phyto material or loose leaf material.

Many herbal vaporization devices on the market utilize a heating chamber in order to heat herbal leaf material in order to vaporize its contents so that desired oils and other flavor materials can be separated from the leaf material in order to be consumed by a user of the device in a vaporized form.

Unfortunately, many of these herbal vaporization devices have long heating times as well as leave the herbal material in contact with the heating chamber of an oven for a prolonged period of time, which may reduce the potency of the vaporization of the desired extracts from the loose leaf herbal materials.

Furthermore, battery life is also important in portable based vaporizers because in some cases users may demand to utilize them over the course of an 8 h day and in some cases if the battery life is too short, then the device will lose its power before the demands of the consumer are met.

Additionally, many vaporization devices on the market utilize proprietary recharging connections, which may not readily be available when on the go. There are also many vaporization devices that utilize non controlled heating of the herbal materials and as a result cause the herbal material to be combusted versus being vaporizer, not to mention that many of these devices are quite bulky in size.

It is therefore an object of the invention to provide an aromatherapy vaporization device that overcomes the aforementioned deficiencies.

SUMMARY

In accordance with the embodiments of the invention there is provided a herbal vaporization device comprising: a recharging unit for storing therein of a vaporization unit comprising a first housing comprising a heating chamber disposed at a first end thereof for receiving of loose leaf herbal material and for providing of heat thereto, the vaporization unit comprising a second end disposed opposite the first end; a conductive heating element disposed proximate the heating chamber at the first end for heating of the loose leaf herbal material for at least partial vaporization thereof; a first battery at least partially disposed within the first housing; a first control circuit coupled with the first battery and the conductive heating element, the first control circuit for controlling the flow of electrical current from the first battery to the conductive heating element; a first battery first recharging contact coupled with the first control circuit and a first battery second recharging contact coupled with the first control circuit, wherein the first and second battery recharging contacts and protrude past the first housing; a switch coupled with the first control circuit for providing a control signal to the first control circuit for affecting the flow of electrical current from the first battery to the conductive heating element; a fluid pathway extending through the housing from the first end to the second end and fluidly coupled with the heating chamber that places the fluid pathway in fluid communication with an outside environment and for allowing of the at least partially vaporized loose leaf herbal material and ambient air to flow therein from proximate the first end to the second end; the recharging unit comprising a second housing for receiving at least partially therein the vaporization unit, the recharging unit having disposed therein a second battery having a larger capacity than the first battery and coupled with a second control circuit and coupled with a recharging port, the recharging port for receiving of electrical energy for recharging of the second battery from an external source; a charging port coupled with the second control circuit for in a first mode of operation for being coupled with the first battery first recharging contact and the first battery second recharging contact for providing of electrical energy from the second battery to the first battery in a controllable manner and for in a second mode of operation for uncoupling of the first battery first recharging contact and the first battery second recharging contact from the charging port, the first and second battery recharging contacts being disposed within the second housing when providing of electrical energy from the second battery to the first battery, wherein in the second mode of operation upon depressing of the switch, electrical current from the first battery is controllably provided to the conductive heating element and the loose leaf herbal material within the heating chamber is heated by the conductive heating element and where upon creating a low pressure proximate the second end, a lower pressure is created in the fluid pathway and ambient air at a higher pressure flows into the heating chamber and propagates through the loose leaf herbal material and vapor emitted from conductive heating of the loose leaf herbal material is mixed with the ambient air and together flows out of the second end.

In accordance with the embodiments of the invention there is provided a herbal vaporization device comprising: a recharging unit for storing therein of a vaporization unit comprising a first housing comprising a heating chamber disposed at a first end thereof for receiving of loose leaf herbal material and for providing of heat thereto, the vaporization unit comprising a second end disposed opposite the first end; a conductive heating element disposed proximate the heating chamber at the first end for heating of the loose leaf herbal material for at least partial vaporization thereof; a first battery at least partially disposed within the first housing; a first control circuit coupled with the first and the conductive heating element, the first control circuit for controlling the flow of electrical current from the first battery to the conductive heating element; a first battery first recharging contact coupled with the first control circuit and a first battery second recharging contact coupled with the first control circuit, wherein the first and second battery recharging contacts protrude past the first housing; a switch coupled with the first control circuit for providing a control signal to the first control circuit for affecting the flow of electrical current from the first battery to the conductive heating element; a fluid pathway extending through the housing from the first end to the second end and fluidly coupled with the heating chamber that places the fluid pathway in fluid communication with an outside environment and for allowing of the at least partially vaporized loose leaf herbal material and ambient air to flow therein from proximate the first end to the second end; a central plane axially propagating from the first end to the second end of the first housing of the vaporization unit, the central plane being disposed equally within a geometric center of first housing, wherein the fluid pathway is offset from the central plane and the heating chamber comprises an aperture that is fluidly coupled with the heating chamber and offset from the central plane, the recharging unit comprising a second housing for receiving at least partially therein the vaporization unit, the recharging unit having disposed therein a second battery having a larger capacity than the first battery and coupled with a second control circuit and coupled with a recharging port, the recharging port for receiving of electrical energy for recharging of the second battery; a charging port coupled with the second control circuit for in a first mode of operation for being coupled with the first battery first recharging contact and the first battery second recharging contact for providing of electrical energy from the second battery to the first battery in a controllable manner and for in a second mode of operation for uncoupling of the first battery first recharging contact and the first battery second recharging contact from the charging port, the first and second battery recharging contacts being disposed within the second housing when providing of electrical energy from the second battery to the first battery, wherein in the second mode of operation upon depressing of the switch, electrical current from the first battery is controllably provided to the conductive heating element and the loose leaf herbal material within the heating chamber is heated by the conductive heating element and where upon creating a low pressure proximate the second end, a low pressure is created in the fluid pathway and ambient air at a higher pressure flows into the heating chamber and propagates through the loose leaf herbal material and vapor emitted from conductive heating of the loose leaf herbal material is mixed with the ambient air and together flows out of the second end.

In accordance with the embodiments of the invention there is provided a method of vaporizing herbal material comprising: a first mode of operation and a second mode of operation; providing a recharging unit comprising a second housing and having disposed therein a second battery having a second capacity and coupled with a second control circuit; providing a vaporization unit comprising a housing having at least partially embedded therein a first battery having a first capacity, the vaporization unit comprising a heating chamber disposed at a first end for receiving of loose leaf herbal material and having a second end with a fluid pathway extending from the first end to the second end thereof; providing a conductive heating element disposed in proximity of the heating chamber proximate the first end; inserting of loose leaf herbal material into the heating chamber; in the first mode of operation, electrically coupling of the first battery with the second control circuit; providing of electrical energy from the second battery to the first battery; in the second mode of operation, electrically uncoupling of the first battery from the second control circuit and physically uncoupling of the vaporization unit from the recharging unit; providing of electrical energy from the first battery to the conductive heating element in a controllable manner; heating of the loose leaf herbal material to generate vapor therefrom; inhaling from the second end of the fluid pathway; creating a reduction in ambient air pressure within the fluid pathway; creating a flow of ambient air to flow past the loose leaf herbal material and mixing with vapor generated as a result of the conductive heating to flow through the fluid pathway; inhaling a mixture of vaporized loose leaf material and ambient air from the second end; removing the loose leaf herbal material from the heating chamber; recoupling electrically of the first battery with the second control circuit; in the first mode of operation, recharging of the first battery from electrical current controllably provided by the second battery through the second control circuit.

DETAILED DESCRIPTION OF EMBODIMENTS OF THE INVENTION

Figure 1A:
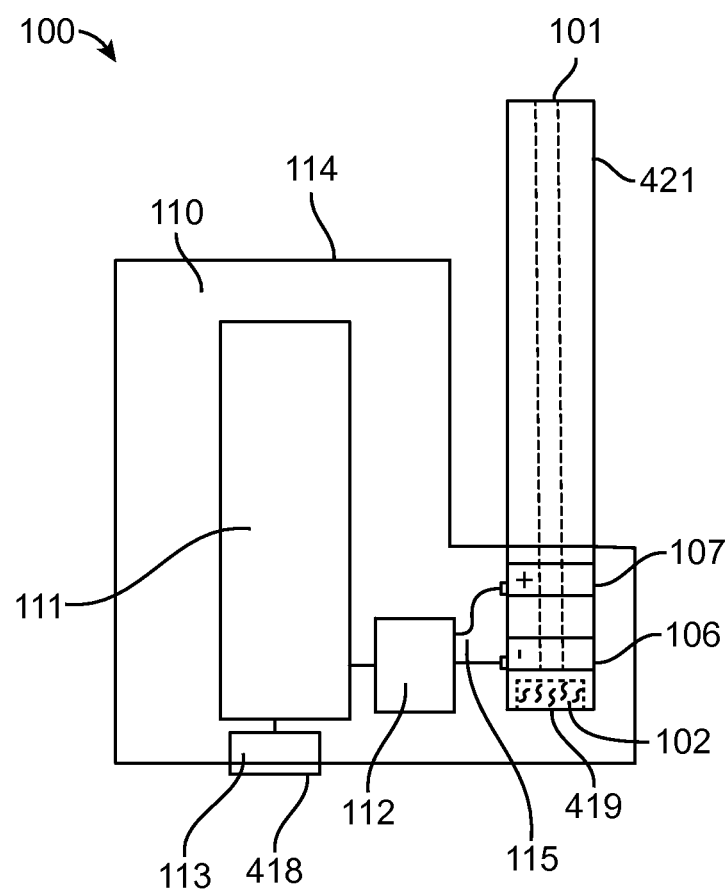
FIG. 1A illustrates a preferred embodiment of the invention, a herbal vaporization device (HVD) in accordance with the preferred embodiment of the invention.

FIG. 1A illustrates a preferred embodiment of the invention, a herbal vaporization device (HVD) 100 in accordance with the preferred embodiment of the invention. The HVD 100 is formed from a recharging unit 110 for storing therein of a vaporization unit 421 having a first housing 101 and having a heating chamber 102 disposed at a first end thereof 101a for receiving of loose leaf herbal material 419 and for providing of heat thereto. The vaporization unit 421 comprising a second end 101b disposed opposite the first end 101a.

Figure 1B:
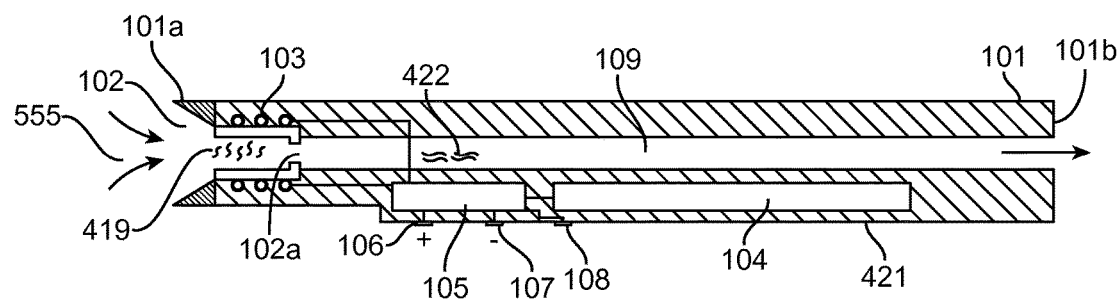
FIG. 1B illustrates a vaporization unit as part of the HVD in more detail in a cutaway view.

Referring to FIG. 1B, a conductive heating element 103 disposed proximate the heating chamber 102 at the first end 101a for heating of the loose leaf herbal material for at least partial vaporization thereof. A first battery 104 is at least partially disposed within the first housing 101 of the vaporization unit 421. A first control circuit 105 is coupled with the first battery 104 and the heating element 103, the first control circuit 105 for controlling the flow of electrical current from the first battery 104 to the heating element 103. A first battery first recharging contact 106 is electrically coupled with the first control circuit 105 and a first battery second recharging contact 107 is electrically coupled with the first control circuit 105, wherein the first and second battery recharging contacts 106 and 107 protrude past the first housing 101.

A switch 108 is electrically coupled with the first control circuit 105 for providing a control signal to the first control circuit 105 for affecting the flow of electrical current from the first battery 104 to the conductive heating element 103. A fluid pathway 109 extends through the housing 101 of the vaporization unit 421 from the first end 101a to the second end 101b and is fluidly coupled with the heating chamber 102 that places the fluid pathway 109 in fluid communication with an outside environment and for allowing of the at least partially vaporized loose leaf herbal material 422 to flow therein from proximate the first end 101a to the second end 101b.

Referring to FIG. 1A, the recharging unit 110 comprising a second housing 114 for receiving at least partially therein the vaporization unit 421, the recharging unit 110 having disposed therein a second battery 111 having a larger capacity than the first battery and coupled with a second control circuit 112 and coupled with a recharging port 113, the recharging port 113 for receiving of electrical energy from an external source (not shown) for recharging of the second battery 111. The external source (not shown) is preferably in the form of a power source, such as a 5 W and 5V USB power supply.

A charging port 115 is electrically coupled with the second control circuit 112 for in a first mode of operation for being coupled with the first battery first recharging contact 106 and the first battery second recharging contact 107 for providing of electrical energy from the second battery 111 to the first battery 104 in a controllable manner and for in a second mode of operation for uncoupling of the first battery first recharging contact 106 and the first battery second recharging contact 107 from the charging port 115, the first and second battery recharging contacts 106, 107 being disposed within the second housing 114 when providing of electrical energy from the second battery 111 to the first battery 104 during the first mode of operation. In the second mode of operation the recharging unit 110 is separated from the vaporization unit 421.

Referring to FIG. 1B, where the vaporization unit 421 is shown in more detail in a cutaway view, loose leaf herbal material 419, the loose leaf herbal material 419 being derived from a phyto material or tobacco, is inserted into the heating chamber and wherein in the second mode of operation upon depressing of the switch 108, electrical current from the first battery 104 is controllably provided to the conductive heating element 103 and the loose leaf herbal material 419 within the heating chamber is heated by the conductive heating element 103 and where upon creating a lower pressure proximate the second end 101b, such as that by an inhalation of a user, a low pressure is created in the fluid pathway 109 and ambient air 555 at a higher pressure flows into the heating chamber 102 and propagates through the loose leaf herbal material 419 and vapor 422 emitted from conductive heating of the loose leaf herbal material is mixed with the ambient air and together flows out of the second end 101b. A heating chamber aperture 102a fluidly couples the heating chamber 102 to the fluid pathway 109.

Advantageously, the first battery 104 is therefore a small battery and smaller in capacity than the second battery 111, for example the first battery is about 300 mAh to 750 mAh and the second battery has a capacity of about 3000 mAh. This allows for the vaporization unit 421 to be relatively small, such as that of a pen. This type of assembly advantageously allows for the first battery 104 to be charged when the vaporization unit 421 has preferably a portion thereof disposed within the recharging unit 110 and the first battery first recharging contact 106 is coupled with the first control circuit 105 and a first battery second recharging contact 107 coupled with the first control circuit 105.

Figure 1C:
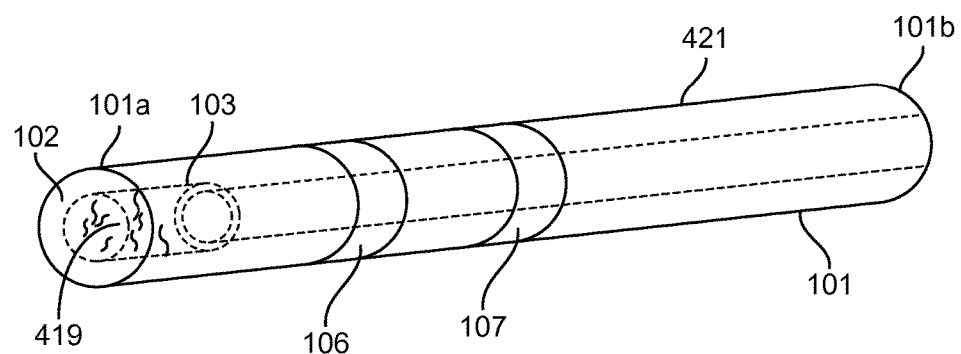
FIG. 1C illustrates the vaporization unit as part of the HVD in a perspective view.

Referring to FIG. 1C, the vaporization unit 421 is shown in perspective, where the first battery first recharging contact 106 and first battery second recharging contact 107 protrude past the housing 101 and substantially wrap around the housing 101 where preferably the housing 101 is cylindrical in shape.

Referring to FIG. 1B, in use, when the loose-leaf material is vaporized, the vapor 422 is for flowing from the first end 101a to the second end 101b where preferably the user has their lips on this end to suck in the vapor being emitted. Once the loose-leaf material has been utilized then it is tapped out from the heating chamber 102 and new material is inserted. Recharging of the first battery 104 will be preferred after a few uses of the vaporization unit 421. In this embodiment the conductive heating element 103 comprises a metallic material and is thermally coupled with an inner surface of the heating chamber 102. Preferably the fluid pathway 109 comprises a thermally conductive material and allows for cooling of the vapor emitted 422 from conductive heating of the loose leaf herbal material 419 and ambient air 555 propagating therethrough.

Figure 1D:
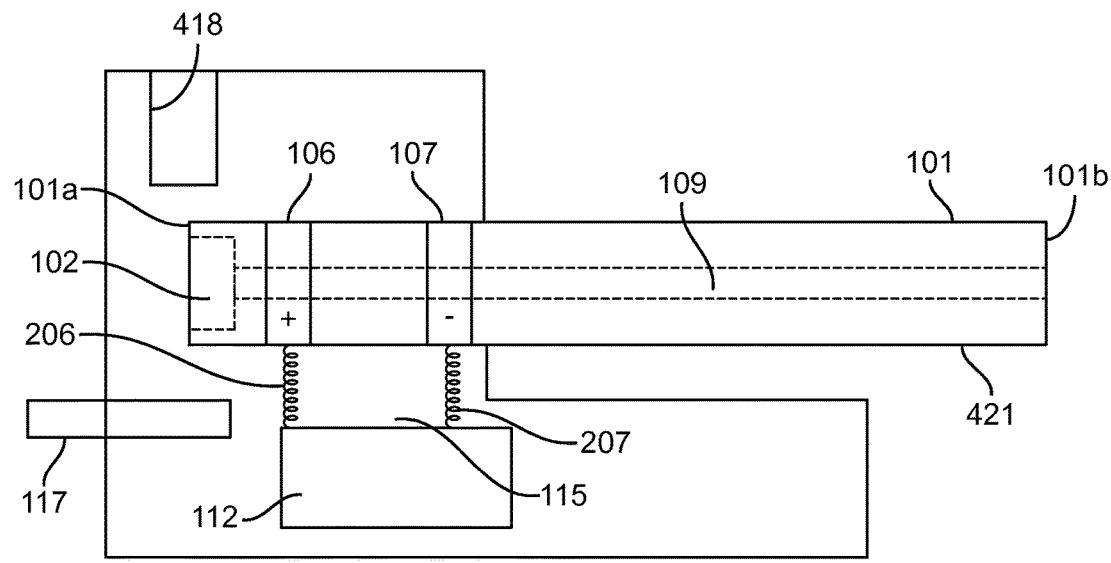
FIG. 1D illustrates an optional storage compartment as part of the recharging unit as well as a detachable cleaning tool.

Referring to FIG. 1D, an optional storage compartment 418 is provided as part of the recharging unit 110 as well as a detachable cleaning tool 117 for cleaning of the heating chamber 102. The second control circuit 112 is electrically coupled with the first battery first recharging contact 106 using a first spring contact 206 and a first battery second recharging contact 107 is electrically coupled with the first control circuit 105 through a second spring contact 207.

The optional storage compartment 418 is for storing of the loose leaf herbal material 419. The heating chamber 102 is thereafter inserted into the optional storage compartment 418 and the loose leaf herbal material 419 is forcefully pushed into the heating chamber 102. The cleaning tool 117 is removed from the recharging unit 110 and used for picking at the loose leaf herbal material 419 once the material has been at least partially vaporized within the heating chamber 102.

Figure 1E:
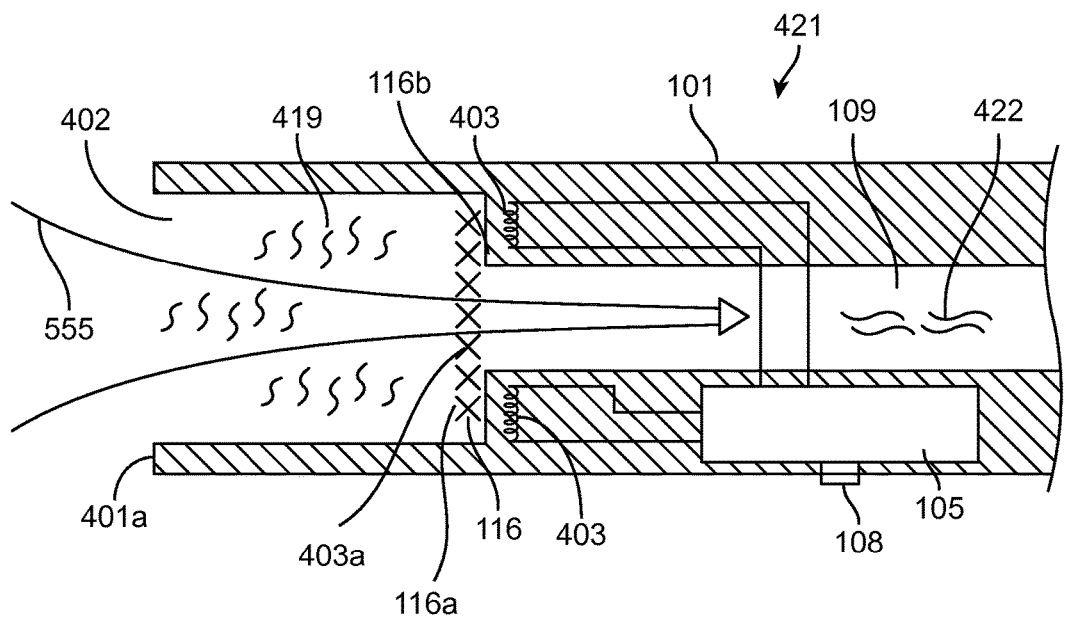
FIG. 1E illustrates an alternate embodiment of the vaporization unit showing a ceramic heating element having an annular shape.

Referring to FIG. 1E, an alternate embodiment of the vaporization unit 421 is shown. It comprises a housing with the heating chamber 402 disposed at a first end 401a for receiving of loose leaf herbal material 419 for providing of heat thereto. In this case the conductive heating element 403 is disposed proximate the heating chamber 402 wherein a screen mesh 116 is disposed between the conductive heating element 403 and the loose leaf herbal material 419. The screen mesh 116 comprising a first side 116a for being in contact with the lose leaf herbal material 419 and a second side 116b for being in contact with the conductive heating element 403, wherein heat emitted from the conductive heating element 403 heats up the screen mesh 116 and heats up the loose leaf herbal material 419 and ambient air 555 and vapor 422 emitted from conductive heating of the loose leaf herbal material 419 propagates through the screen mesh 116.

In this embodiment the conductive heating element 403 is disposed within the heating chamber 402 and the heating chamber is manufactured from other them a metallic material, such as a ceramic material. Preferably the screen mesh 116 comprises a metal material and allows for heating of the screen mesh 116 through the conductive heating element 403. The conductive heating element 403 is disposed within the heating chamber 402.

Referring to FIG. 1E, the conductive heating element 403 is in the form of a ceramic heating element having an annular shape with a center of the ceramic heating element forming an aperture 403a and being in fluid communication with the fluid pathway 109 and for allowing of ambient air 555 and vapor 422 emitted from conductive heating of the loose leaf herbal material to flow together through the aperture 403a of the annular shape ceramic heating element.

Preferably in order to effectively reduce heat generated from vaporization of the loose leaf herbal material 419, the fluid pathway 109 is thermally conductive and has an ability to transfer heat across the material at a generally high rate. Preferably the fluid pathway 109 is made from a metal, such as aluminum or copper. Optionally the fluid pathway 109 is made from conductive polymers, composites, or other metallic-based materials with thermally conductive properties. As the ambient air 555 is directed through the loose leaf herbal material 419 proximate the first end 101a and propagates with the ambient air through the fluid pathway 109 extending through the housing 101 from the first end 101a to the second end 101b, where it is subsequently inhaled by a user, a temperature thereof has been reduced to a range that is safe and comfortable for the user to inhale.

Figure 2A:
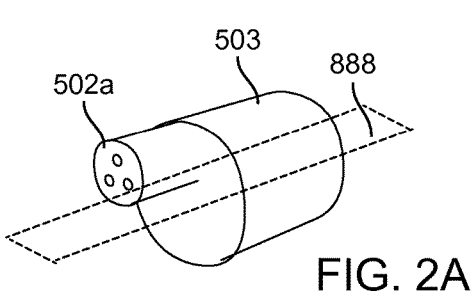
FIG. 2A illustrates a heating chamber and conductive heating element from a perspective rear view.
Figure 2B:
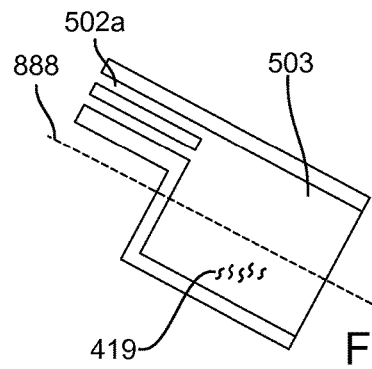
FIG. 2B illustrates a heating chamber and conductive heating element from a cutaway view.
Figure 2C:
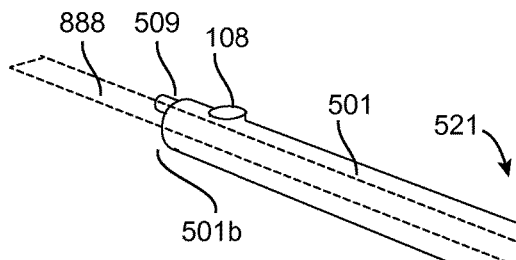
FIG. 2C illustrates a vaporization unit in accordance with another embodiment of the invention.
Figure 2D:
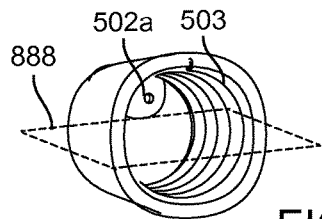
FIG. 2D illustrates a heating chamber and conductive heating element from a front perspective view; and, FIG. 2E illustrates the vaporization unit in accordance with another embodiment of the invention having a housing removed.

Referring to FIGS. 2C and 2D a vaporization unit 521 in accordance with another embodiment of the invention is shown. This herbal vaporization device is formed from a recharging unit 110 (see FIG. 1A) and the vaporization unit 521 of FIGS. 2C and 2D. The recharging unit 110 (see FIG. 1A) is for storing therein at least partially the vaporization unit 521 comprising a first housing 501 comprising a heating chamber 502 disposed at a first end thereof 501a for receiving of loose leaf herbal material 419 and for providing of heat thereto, the vaporization unit 521 comprising a second end 501b disposed opposite the first end 501a. The vaporization unit 521 does not tether to the recharging unit 110 and couples directly therewith, therefore allowing for a more compact HVD 100 and provides for improved ease of use.

A conductive heating element 503 is disposed proximate the heating chamber 502 at the first end 501a for heating of the loose leaf herbal material 419 for at least partial vaporization thereof. A first battery 104 is at least partially disposed within the first housing 501 and a first control circuit 105 is coupled with the first battery 104 and the conductive heating element 503, the first control circuit 105 for controlling the flow of electrical current from the first battery 104 to the conductive heating element 503.

Referring to FIGS. 1A and 2C, a first battery first recharging contact 106 coupled with the first control circuit 105 and a first battery second recharging contact 107 coupled with the first control circuit 105, wherein the first and second battery recharging contacts 106 and 107 protrude past the first housing 501. A switch 108 is coupled with the first control circuit 105 for providing a control signal to the first control circuit 105 for affecting the flow of electrical current from the first battery 104 to the conductive heating element 503 (FIGS. 2A, 2B and 2D).

Figure 2E:
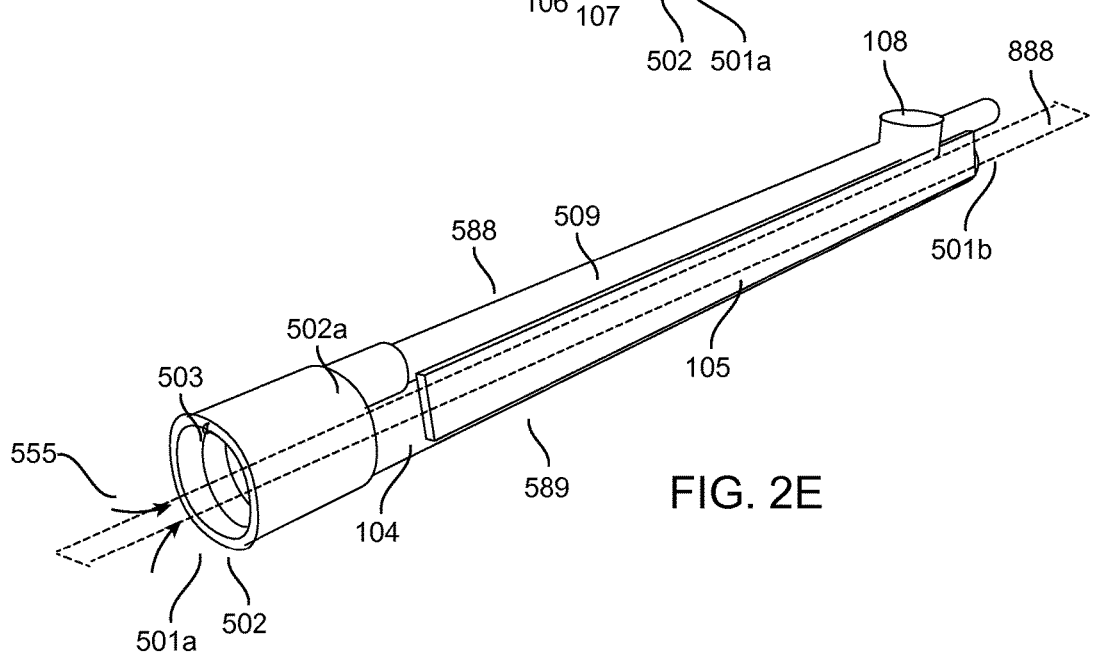

Referring to FIG. 2E, a fluid pathway 509 extends through the housing 501 (shown in FIG. 2C) from the first end 501a to the second end 501b and fluidly coupled with the heating chamber 502 that places the fluid pathway 509 in fluid communication with an outside environment and for allowing of the at least partially vaporized loose leaf herbal material 419 and ambient air 555 to flow therein from proximate the first end 501a to the second end 501b.

A central plane 888 axially propagates from the first end 501a to the second end 501b of the first housing 501 of the vaporization unit 521, the central plane 888 being disposed equally within a geometric center of first housing 501, wherein the fluid pathway 509 (FIG. 2E) is offset from the central plane 888 and the heating chamber 502 comprises an aperture 502a (FIG. 2A) that is fluidly coupled with the heating chamber 502 and offset from the central plane 888.

Referring to FIG. 1A in combination with FIG. 2C, the recharging unit 110 comprising a second housing 114 for receiving at least partially therein the vaporization unit 521, the recharging unit 110 having disposed therein a second battery 111 having a larger capacity than the first battery 104 and coupled with a second control circuit 112 and coupled with a recharging port 113, the recharging port 113 for receiving of electrical energy for recharging of the second battery 111.

In the second mode of operation upon depressing of the switch 108, electrical current from the first battery 104 is controllably provided to the conductive heating element 503 and the loose leaf herbal material 419 within the heating chamber 502 (FIG. 2B) is heated by the conductive heating element 503 and where upon creating a low pressure proximate the second end 501b, a lower pressure is created in the fluid pathway 509 and ambient air at a higher pressure flows into the heating chamber 502 and propagates through the loose leaf herbal material 419 and vapor emitted from conductive heating of the loose leaf herbal material 419 is mixed with the ambient air and together flows out of the second end 501b.

Referring to FIG. 2E, the vaporization unit 521 comprise a first portion 588 and a second portion 599, wherein the first portion 588 and second portion 589 are separated by the central plane 888 and the first portion 588 comprises the switch 108 and the fluid pathway 509 wherein the second portion 599 comprises the first battery 104.

Referring to FIG. 2E, The first portion 588 comprises the fluid pathway 509 and the heating chamber 502 comprises the aperture 502a that is fluidly coupled with the heating chamber 502, wherein in use, in the second mode of operation the central plane 888 is oriented with the first end 501a closer relative to ground than the second end 501b (FIG. 2C) where a partial amount of vapor emitted from conductive heating of the loose leaf herbal material 419 rises from the second portion 589 to the first portion 588 for flowing through the aperture 502a and into the fluid pathway 509. Because the vapor emitted from the conductive heating of the loose leaf herbal material is hotter than ambient air, it will tend to rise.

Preferably the fluid pathway 509 comprises a thermally conductive material and allows for cooling of the vapor emitted from conductive heating of the loose leaf herbal material and ambient air propagating therethrough. Referring to FIG. 2C, the heating chamber 502 comprises other than a metal material and comprises a ceramic material and the conductive heating element 503 is formed as a unitary construction with the heating chamber 502. This is advantageous from a manufacturing standpoint as it allows for the manufacturing of the conductive heating element 503 and the heating chamber 502 as a single unit that has electrical connections for being connected to the first control circuit 105.

Referring to FIGS. 1A, 1C and 1D, a method of vaporizing herbal material is disclosed. The method comprises providing a recharging unit 110 comprising a second housing 114 and having disposed therein a second battery 111 having a second capacity and coupled with a second control circuit 112. It includes providing a vaporization unit 421 comprising a housing 101 having at least partially embedded therein a first battery having a first capacity, the vaporization unit comprising a heating chamber 102 disposed at a first end 101*a* for receiving of loose leaf herbal material 419 and having a second end 101*b* with a fluid pathway 109 extending from the first end 101*a* to the second end 101*b* thereof. A conductive heating element 103 is provided and disposed in proximity of the heating chamber 102 proximate the first end 101*a*. Loose leaf herbal material 419 is inserted into the heating chamber and in the first mode of operation, electrically coupling of the first battery 104 with the second control circuit 112. Providing of electrical energy from the second battery 111 to the first battery 104. In the second mode of operation, electrically uncoupling of the first battery 104 from the second control circuit 112, physically uncoupling of the vaporization unit 521 from the recharging unit 110 and providing of electrical energy from the first battery 104 to the conductive heating element 103 in a controllable manner. This results in heating of the loose leaf herbal material 419 to generate vapor 422 therefrom for inhaling from the second end of the fluid pathway 109 by the user. This results in a creation of a reduction in ambient air pressure within the fluid pathway 109 and creates a flow of ambient air 555 to flow past the loose leaf herbal material 419 and mixing with vapor generated as a result of the conductive heating to flow through the fluid pathway 109.

The user inhales a mixture of vaporized loose leaf material 422 and ambient air 555 from the second end 101*b*. Upon completion, removing the loose leaf herbal material 419 from the heating chamber is performed. Re-coupling electrically of the first battery 104 with the second control circuit 112 is achieved and in the first mode of operation, recharging of the first battery 104 from electrical current controllably provided by the second battery 111 through the second control circuit 112.

Advantageously, the embodiments of the invention allow for the loose leaf herbal material, such as tobacco, to be loaded into the heating chamber proximate the first end of the vaporization unit and to be enjoyed in small doses where it is vaporize as opposed to being burned. Optionally the temperature at which the material is vaporized is adjustable. Advantageously, by having a small heating chamber a short heating time is provided for heating of the loose-leaf materials.

Advantageously because of small battery the form factor of the vaporization unit 421 is small and it may only provide enough current in the first battery 104 for one or two full cycles of heating of the loose leaf herbal material 419 prior to require charging of the vaporization unit 412 first battery 104 using the second battery 111. Having a small battery capacity for the first battery 104 allows for the first housing 101 to be compact in size and thus having an advantage to the user they are not exhibiting a large herbal vaporization device.

Furthermore, because of having a small sized heating chamber as well as having two batteries, the first and the second battery, the battery life can therefore be extended to preferably meet the demands of the consumer. Furthermore, a capacity of the second battery is larger than a capacity of the first battery. For example the first battery has a capacity of 500 mAH and the second battery has a capacity of 2700 mAh. Thus the second battery facilitates multiple recharges of the first battery.

Numerous other embodiments are envisaged without departing from the spirit or scope of the invention.

What I claim is:

1. A herbal vaporization device comprising:
   a vaporization unit comprising
   a first housing comprising a first end, a second end disposed opposite the first end, and a heating chamber disposed at the first end for receiving loose leaf herbal material and for providing heat to the loose leaf herbal material;
   a conductive heating element disposed proximate the first end of the heating chamber for heating the loose leaf herbal material for at least partial vaporization of the loose leaf herbal material;
   a first battery at least partially disposed within the first housing;
   a first control circuit coupled with the first battery and the conductive heating element, the first control circuit for controlling the flow of electrical current from the first battery to the conductive heating element;
   a first battery first recharging contact coupled with the first control circuit and a first battery second recharging contact coupled with the first control circuit, wherein the first and second battery recharging contacts protrude from the first housing;
   a switch coupled with the first control circuit for providing a control signal to the first control circuit for affecting the flow of electrical current from the first battery to the conductive heating element; and
   a fluid pathway extending through the housing from the first end to the second end, the fluid pathway being fluidly coupled with the heating chamber thereby placing the fluid pathway in fluid communication with an outside environment and allowing the at least partially vaporized loose leaf herbal material and ambient air to flow through the fluid pathway from proximate the first end to the second end;
   wherein the first housing defines a central axis extending from the first end to the second end of the first housing and a central plane positioned to contain a line coincident with the central axis, wherein the fluid pathway is offset from the central plane and the heating chamber comprises an aperture that is fluidly coupled with the fluid pathway, and the aperture is also offset from the central plane; and
   a recharging unit comprising
   a second housing for receiving at least partially therein the vaporization unit, the recharging unit having disposed therein a second battery having a larger capacity than the first battery, the second battery being coupled with a second control circuit and coupled with a recharging port, the recharging port for receiving electrical energy for recharging of the second battery; and
   a charging port coupled with the second control circuit, wherein, in a first mode of operation, the charging port is coupled with the first battery first recharging contact and the first battery second recharging contact to provide electrical energy from the second battery to the first battery in a controllable manner and, wherein, in a second mode of operation, the charging port is uncoupled from the first battery first recharging contact and the first battery second recharging contact, the first battery first recharging contact and the first battery second battery recharging contact being disposed within the second housing in the first mode of operation, wherein, in the second mode of operation, upon depressing of the switch, electrical current from the first battery is controllably provided to the conductive heating element and the loose leaf herbal material within the heating chamber is heated by the conductive heating element and where upon creating a low pressure proximate the second end, a low pressure is created in the fluid pathway and ambient air at a higher pressure flows into the heating chamber and propagates through the loose leaf herbal material and vapor emitted from conductive heating of the loose leaf herbal material is mixed with the ambient air and together flows out of the second end.

2. A herbal vaporization device according to claim 1, wherein the vaporization unit comprises a first portion and a second portion, wherein the first portion and second portion are separated by the central plane, and the first portion comprises the switch and the fluid pathway, and wherein the second portion comprises the first battery.

3. A herbal vaporization device according to claim 1, wherein the vaporization unit comprises a first portion and a second portion, wherein the first portion and second portion are separated by the central plane with the first portion positioned on a first side of the central plane and the second portion positioned on a second side of the central plane, and the first portion comprises the fluid pathway and the aperture of the heating chamber, wherein, in use, in the second mode of operation at least some of the vapor emitted from conductive heating of the loose leaf herbal material flows from the second portion to the first portion, passes through the aperture of the heating chamber and flows into the fluid pathway.

4. A herbal vaporization device according to claim 2, wherein the fluid pathway comprises a thermally conductive material and allows for cooling of the vapor emitted from conductive heating of the loose leaf herbal material and ambient air propagating therethrough.

5. A herbal vaporization device according to claim 1, wherein the heating chamber comprises other than a metal material and comprises a ceramic material and the conductive heating element is formed as a unitary construction with the heating chamber.

6. A herbal vaporization device according to claim 1, wherein the conductive heating element comprises a metallic material and the conductive heating element is thermally coupled with an inner surface of the heating chamber.

7. A herbal vaporization device according to claim 1, wherein the conductive heating element is a ceramic heating element having an annular shape and the conductive heating element is thermally coupled with an inner surface of the heating chamber.

8. A herbal vaporization device according to claim 1, wherein the recharging unit further comprises a detachable cleaning tool usable to clean the heating chamber.

9. A herbal vaporization device according to claim 1, wherein the recharging unit further comprises a storage compartment usable to store the loose leaf herbal material.

10. A herbal vaporization device according to claim 1, wherein the first battery has a first battery capacity, the second battery has a second battery capacity, and the second battery capacity is at least four times the first battery capacity.

11. A herbal vaporization device according to claim 10, wherein the second battery capacity is at least ten times the first battery capacity.

12. A herbal vaporization device according to claim 1, wherein the first battery has a capacity between 300 mAh and 750 mAh.

13. A herbal vaporization device according to claim 1, wherein the second battery has a capacity of at least 3000 mAh.

* * * * *